United States Patent
Pinhasi et al.

(10) Patent No.: US 11,835,473 B2
(45) Date of Patent: Dec. 5, 2023

(54) METHOD AND DEVICE FOR GRADING DIAMONDS USING RADIOFREQUENCY (RF) SPECTROSCOPY

(71) Applicant: ARIEL SCIENTIFIC INNOVATIONS LTD., Ariel (IL)

(72) Inventors: Yosef Pinhasi, Tel Aviv (IL); Asher Yahalom, Givaat Shmuel (IL); Haim Cohen, Beit-Hashmonai (IL); Avner Cahana, Kfar Trumann (IL); Yossi Rabinovich, Etz Efraim (IL); Boris Litvak, Maale Adumim (IL); Ariel Etinger, Ariel (IL)

(73) Assignee: ARIEL SCIENTIFIC INNOVATIONS LTD., Ariel (IL)

( * ) Notice: Subject to any disclaimer, the term of this patent is extended or adjusted under 35 U.S.C. 154(b) by 690 days.

(21) Appl. No.: 17/040,617

(22) PCT Filed: Mar. 20, 2019

(86) PCT No.: PCT/IL2019/050315
§ 371 (c)(1),
(2) Date: Sep. 23, 2020

(87) PCT Pub. No.: WO2019/180718
PCT Pub. Date: Sep. 26, 2019

(65) Prior Publication Data
US 2021/0116394 A1    Apr. 22, 2021

Related U.S. Application Data

(60) Provisional application No. 62/647,567, filed on Mar. 23, 2018.

(51) Int. Cl.
*G01N 22/02* (2006.01)
*G01N 27/24* (2006.01)
(Continued)

(52) U.S. Cl.
CPC .............. *G01N 22/02* (2013.01); *G01N 27/24* (2013.01); *G01N 27/82* (2013.01); *G01N 33/381* (2013.01)

(58) Field of Classification Search
CPC ........ G01N 22/02; G01N 27/24; G01N 27/82; G01N 33/381
(Continued)

(56) References Cited

U.S. PATENT DOCUMENTS

| 5,559,436 A | 9/1996 | Matthews et al. |
| 6,265,884 B1 | 7/2001 | Menashi et al. |

(Continued)

FOREIGN PATENT DOCUMENTS

| EP | 0424167 A2 | 4/1991 |
| GB | 2239519 A | 7/1991 |

OTHER PUBLICATIONS

A. T. Collins et al in "High-temperature annealing of optical centres in type-I diamond", Journal of Applied Physics, 97(8), pp. 083517-1-10. (2015).

(Continued)

*Primary Examiner* — Nicole M Ippolito
(74) *Attorney, Agent, or Firm* — The Roy Gross Law Firm, LLC; Roy Gross

(57) ABSTRACT

The present invention describes a device and a method for grading diamonds using electromagnetic fields with a radiofrequency or terahertz frequency. The method for grading diamonds comprises placing the diamond (4) into a grading device, applying an electromagnetic field with a frequency range of up to 30 THz to the diamond, recording a modulated signal received from the diamond in a form of S-parameters as a function of frequency or any other parameter that can be deduced by applying said electromagnetic field, processing the recorded signal in the processing unit to (Continued)

Diamond Grade Output obtain data containing information about either an amplitude, or phase, or both of the recorded S-parameters as a function of frequency or said any other parameter, performing calculations relating to the obtained data, and running a computer algorithm correlating the calculated data to either nitrogen concentration, boron concentration or plastic deformation in diamonds, thereby allowing grading of the diamond. The device comprises the following components, RF generator (1), transmitting antenna (2), waveguide (3), receiving antenna (5), amplitude and frequency detector (6) and computing unit (7).

14 Claims, 14 Drawing Sheets
(10 of 14 Drawing Sheet(s) Filed in Color)

(51) Int. Cl.
*G01N 27/82* (2006.01)
*G01N 33/38* (2006.01)

(58) Field of Classification Search
USPC .................................................. 250/492.1
See application file for complete search history.

(56) References Cited

U.S. PATENT DOCUMENTS

| | | | |
|---|---|---|---|
| 7,388,656 B2 | 6/2008 | Liu | |
| 7,652,755 B2 | 1/2010 | Liu | |
| 2005/0068047 A1* | 3/2005 | Claus | G01N 27/221 |
| | | | 324/693 |

OTHER PUBLICATIONS

S. R. Boyd et al in "Multiple growth events during diamond genesis: an integrated study of carbon and nitrogen isotopes and nitrogen aggregation state in coated stones", Earth and Planetary Science Letters, 86, pp. 341-353. (1987).

S. Eaton-Magaña et al; "An Introduction to Photoluminescence Spectroscopy for Diamond and Its Applications in Gemmology", Gems & Gemmology, vol. 52, No. 1, pp. 2-17. (2016).

K. H. Hu et al in "Simple Amplitude and Phase Detector for Accelerator Instrumentation", AIP Conference Proceedings 648, pp. 523-530. (2002).

International Search Report of PCT/IL2019/050315 Completed Jun. 27, 2019; dated Jul. 8, 2019 5 Pages.

Written Opinion of PCT/IL2019/050315 Completed Jun. 27, 2019; dated Jul. 8, 2019 5 Pages.

\* cited by examiner

METHOD AND DEVICE FOR GRADING DIAMONDS USING RADIOFREQUENCY (RF) SPECTROSCOPY

CROSS REFERENCE TO RELATED APPLICATIONS

This application is a National Phase of PCT Patent Application No. PCT/IL2019/050315 having International filing date of Mar. 20, 2019, which claims the benefit of priority of U.S. Provisional Application No. 62/647,567 filed on Mar. 23, 2018. The contents of the above applications are all incorporated by reference as if fully set forth herein in their entirety.

TECHNICAL FIELD

The present application relates to the field of grading diamonds. In particular, the present application relates to device and method for grading diamonds using electromagnetic fields, such as radiofrequency spectroscopy in the terahertz (THz) range and below, including direct current.

BACKGROUND

Diamonds come in a variety of colours, and some of them, such as pink, blue or yellow, are highly prized. However, in a colourless diamond, the presence of a colour tint is considered a defect of the diamond and significantly lowers its price. Very pure colourless diamonds have no body colour, hence the greater value they have. Looking at rough diamonds it is difficult to determine the colour that they will have after polishing. A diamond's origin, whether it was mined from the earth or synthesised in a lab and subsequent treatment history can be a major factor in its value.

Diamonds are classified based on their colour and physical properties, which helps to form the basis of the identification of natural, synthetic and treated diamonds. Diamonds are composed of essentially pure carbon. However, they also contain trace elements, such as nitrogen or in rare cases boron and also defects acquired naturally during the course of formation. The colour of diamonds is originated from their atomic-scale features (often termed optical centres, optical defects, or simply defects) that occur within the diamond structure. These defects may include mainly the aforementioned trace atoms of nitrogen. In other diamonds, trace elements are added as the result of treatment or synthesis in a laboratory. However, diamonds may also contain other imperfections in the lattice of carbon atoms, often termed as lattice defects. These imperfections are vacant carbon-atom locations (holes or vacancies) or plastic deformations in crystal lattices of diamonds. The configuration of these defects and their concentration vary with the growth conditions and subsequent geological or treatment history.

All diamonds are divided into two types based on the presence or absence of nitrogen atoms within the crystal lattices. The most common Type I diamonds contain nitrogen atoms as their main impurity, commonly at a concentration of 0.1%. Type I diamonds absorb in both the infrared and ultraviolet region above 320 nm. They may also have a characteristic fluorescence and visible absorption spectrum.

Type II diamonds have no measurable nitrogen atoms in the lattices. These diamonds therefore absorb in a different region of the infrared and transmit in the ultraviolet below 225 nm. They also have different fluorescence characteristics, but no discernible visible absorption spectrum. The crystals as found tend to be large and irregular in shape. Type II diamonds were formed under extremely high pressure for longer time periods.

These two types are further subdivided into several other types based on arrangement of the trace elements in crystal lattices. For example, Type Ia diamonds, which constitute approximately 95% of natural diamonds, contain nitrogen atoms in clusters and normally vary from near-colourless to light yellow. These "cape" diamonds derived their name from diamonds that were initially mined in Cape Province, South Africa. Sub-type IaA diamonds contain nitrogen atoms aggregated in pairs, while sub-type IaB diamonds contain clusters of four nitrogen atoms surrounding a central lattice carbon vacancy. Most blue-grey diamonds coming from the Argyle mine of Australia are probably of IaB type.

Type Ib diamonds also contain nitrogen, but as isolated atoms instead of clusters. These nitrogen atoms are more diffuse and dispersed throughout the crystal in isolated sites. Type Ib diamonds are often bright yellow in colour and are extremely rare. The trade sometimes refers to these colours as "canary". These diamonds absorb green light in addition to blue and have a much more intense or darker yellow or brown colour than Type Ia diamonds. Almost all synthetic diamonds manufactured in the high pressure high temperature (HPHT) method are of Type Ib.

Type IIa diamonds have no measurable nitrogen or boron impurities and chemically are the purest diamonds with the highest thermal conductivity. They are very transparent in ultraviolet with no absorption above 230 nm. These diamonds are usually colourless but they can also be grey, light brown, light yellow or light pink. Their occasional colour is probably a result of plastic deformations. While Type IIa diamonds are being extruded towards the surface of the Earth, the pressure and tension could cause structural anomalies arising through the plastic deformation during the growth of the tetrahedral crystal structure, leading to imperfections. These imperfections can confer the different colours to the stones. A. T. Collins et al in "*High-temperature annealing of optical centres in type-I diamond*", Journal of Applied Physics, 97(8), (2015), pp. 083517-1-10 describes the HPHT process for repairing the structural deformations in the Type IIa diamonds, removing much or all of the diamond's colour. Type IIa diamonds constitute a great percentage of Australian production. Many famous large diamonds, like the Cullinan, Koh-I-Noor, and Lesedi La Rona, are Type IIa. Synthetic diamonds grown using chemical vapour deposition (CVD) process typically also belong to this type.

Type IIb diamonds contain boron impurities making them one of the rarest natural diamonds and extremely valuable. The trace element boron is responsible for most of them being light blue or greyish blue, because the absorption spectrum of boron causes these stones to absorb red, orange, and yellow light, though examples with low levels of boron impurities can also be colourless. The historic Wittelsbach Blue diamond was sold for a record-breaking $24.3 million to London jeweller Laurence Graff at Christie's in December 2008. It was consequently recut to 31.06 carat and renamed the Wittelsbach-Graff. Type IIb diamonds show distinctive infrared absorption spectrum and show gradually increasing absorption towards the red side of visible spectrum. These diamonds are also p-type semiconductors, unlike other diamond types, due to uncompensated electron holes. Therefore, they are known to conduct electricity. As little as 1 ppm of boron is enough for this effect.

Every diamond on the market is assigned a colour grade that is certified by a skilled person or a gemological laboratory. This allows the colour of a diamond to be accurately measured and graded for determining its price on the market. Minor differences in the diamond colour graded in the laboratories are very difficult if not impossible to detect outside of these laboratories. The diamond industry has adopted the common international colour scale of diamonds, and almost every diamond sold today is rated using this colour scale. Identification of the diamond type, also known as grading, is critical. With increasing availability and complexity of treated and synthetic diamonds, any diamond professional will surely benefit from adequate diamond type identification, enhancing consumer confidence.

The scale for grading diamonds is from D (colourless) to Z (light colour), where the difference in colour between D, E and F is negligible and can be detected only by a gemologist in side by side comparisons. The G, H, I and J grades are considered near-colourless or having slight traces of colour that are not easily detectable to the untrained eye, particularly when the diamonds are placed in a mounting or frame. Down the scale, the traces of colour in a diamond become gradually more apparent. Starting from K diamonds, the colour having usually a yellow tint is easily detected by the naked eye. The K, L and M diamonds are therefore said to have "faint" colours, while diamonds in the colour range from N to R have an easily seen yellow or even brown tint and are significantly less expensive than higher grades. In general, almost all D to Z diamonds are considered colourless, even though they contain varying degrees of colour. True fancy coloured diamonds, such as pink and blue, are graded on a separate colour scale.

Polished single diamonds are much easier to grade than rough (unpolished) diamonds. A rough diamond is barely transparent which results in its possibly incorrect grading and consequently, heavy material losses to a diamond dealer purchasing such rough diamond. Spectroscopic techniques for grading diamonds discussed below are based on transmission of UV or IR light through diamonds and therefore, normally fail in grading such diamonds, simply because UV or IR light is not able to pass the unpolished or impure diamonds without much optical interference.

In manual grading, there are master stones available for colour comparison. Many graders grade diamonds using such set of master stones. This set of pre-graded master stones usually consist of five diamonds in two grade increments e.g. E, G, I, K and M. Each master stone represents the least amount of colour for that range. In other words, each stone shows the least amount of body colour that the grade colour could exhibit and will be compared to the diamond being assessed. In general, diamonds have a range of colours within one colour. For example, two H-colour diamonds can be in entirely different ranges of the H colour. One may be exactly the same H colour as the master stone H and the other may have a deeper H colour. The intermediate grades are usually assessed according to the grader's own judgement. This is a largely subjective process however, and is dependent upon the grader's skill in this area.

Due to complex treatments and the evolution of synthetic diamond growth techniques, the accurate assessment of colour origin is best left to fully equipped gemological laboratories. There are several devices which are used by laboratories to aid determining diamond colour grades. The approach and equipment used differs from one laboratory to another. The Gran Colorimeter, for example, can very accurately and impartially determine a diamond colour, and is even able to produce results which impart how high or low the diamond is in this grading category. Major instruments which are used today to grade diamonds are spectroscopic units in the visible-UV or the infrared range to measure the absorption spectrum of the diamond.

Fluorescence spectroscopy is used for characterisation of diamonds which are capable of emitting fluorescence when exposed to ultraviolet light. However, this is not a common trait and only about 30% of diamonds exhibit this characteristic to some degree. In addition, because fluorescent glow is usually blue (complementary colour to yellow), diamonds of I-M colour having a blue fluoresce tend to appear to one grade whiter when exposed to daylight. As a result, if a lower-colour diamond with strong fluorescence is chosen, the stone will appear to be more colourless than it is as some of the yellow body colour is cancelled out in the daylight. For this reason, I-M diamonds tend to sell at a slight premium when they possess medium to very strong fluorescence, but colourless (D-F) diamonds having fluorescence sell at up to a 15% discount since fluorescence is perceived as a defect. Overall, diamond fluorescence cannot be a major factor in grading diamonds for the above reasons.

The emergence of more complex grading techniques for diamonds and the development of sophisticated synthetic diamonds have meant that the use of standard gemological techniques described above cannot entirely guarantee the identity and quality of a stone. For this reason, new advanced spectroscopic techniques for grading diamonds have recently been developed. U.S. Pat. Nos. 7,652,755 and 7,388,656 by LiuLabs describe multifunction dual integrating sphere spectrometer for grading diamonds controlled by artificial intelligence software with several functions of spectral measurement, colour measurement, fluorescence measurement, photoluminescence measurement, colour grading of diamonds, colour grading of coloured diamonds, colour grading of jadeite, and alexandrite effect grading.

Another spectroscopic technique that has recently and intensively been used in grading diamonds is Fourier-Transform Infrared Spectroscopy (FTIR). It analyses the vibrational spectrum of molecules, with each functional group in a molecule having its characteristic wave numbers. This is a non-destructive analysis technique which can be used at room temperature or if needed at liquid nitrogen temperature (especially when investigating diamonds). FTIR produces spectra for each analysed sample, and these spectra are then compared to known spectra in a reference library. FTIR can be used in grading diamonds in a number of different scenarios including identifying diamond type, investigating spectra indicative of a particular coloured diamond, or investigating if a coloured diamond has been treated for colour. As the measured FTIR spectrum is directly related to the chemical structure and composition of a diamond, it provides a reliable characterisation and identification of the diamond. Impurities within a diamond (nitrogen and boron) give unique signatures in the FTIR spectrum, which can be used for characterisation of the different types of diamonds.

S. R. Boyd et al in "*Multiple growth events during diamond genesis: an integrated study of carbon and nitrogen isotopes and nitrogen aggregation state in coated stones*", Earth and Planetary Science Letters, 86, (1987), pp. 341-353, described the combination of dynamic and high-sensitivity static mass spectrometry with high-resolution technique to investigate the variance of carbon and nitrogen isotope composition, nitrogen concentration and the degree of nitrogen aggregation within diamonds, employing microgram-sized samples.

Raman spectroscopy, which is a form of vibrational spectroscopy that can be used to analyse very small samples, is also a non-destructive testing technique and is very reliable in identifying a diamond by comparing its spectrum to known spectra in a reference library. This can also be done at room temperature or at liquid nitrogen temperature. Raman spectroscopy can be successfully used in combination with FTIR for grading diamonds. In a photoluminescence mode, a Raman spectrometer is capable of identifying synthetic diamonds and Type II diamonds that have been treated to produce a very high colour grade. Although Raman provides different information from FTIR, as the physical way that the techniques analyse a sample spectrum is different, their results are often considered in combination and can provide the final answer regarding a diamond.

S. Eaton-Magaña and C. Breeding in "*An Introduction to Photoluminescence Spectroscopy for Diamond and Its Applications in Gemmology*", Gems & Gemmology, Spring 2016, Vol. 52, No. 1, pp. 2-17, reviewed a photoluminescence spectroscopy for grading diamonds. It is a non-destructive analytical technique in which a diamond is illuminated with UV light and the resulting luminescence is recorded as a plot of emitted light intensity versus wavelength. In the last decade, photoluminescence has become an essential tool used by major gemological laboratories to separate treated and synthetic diamonds from their natural counterparts.

Notwithstanding the aforementioned developments in optical spectroscopy for grading diamonds, the problems of incorrect grading of rough diamonds having reduced transparency, difficulty to separate treated and synthetic diamonds from their natural counterparts and to identify plastic deformation in diamonds still persist. These problems lead to only about 70-85% of diamonds being graded correctly today. Therefore, there is a long-felt need to significantly improve the grading of rough and polished diamonds, to identify plastic deformation in diamonds, and to separate treated and synthetic diamonds from their natural counterparts. These problems are addressed by the present invention.

SUMMARY

The present application describes embodiments of a method for grading a diamond comprising the steps of:
a) Placing the diamond to be graded into a grading device;
b) Applying an electromagnetic field (EM) to the diamond within the grading device;
c) Recording a modulated signal received from the diamond, after applying the EM field in a form of S-parameters as a function of frequency or any other parameter, such as complex dielectric constant, complex magnetic permeability, capacitance, inductance, resistance, reflectance, absorbance, or any other parameter that can be deduced by applying said EM field;
d) Processing the recorded signal in the processing unit to obtain data containing information about either an amplitude, or phase, or both of the recorded S-parameters as a function of frequency or said any other parameter;
e) Performing calculations relating to mathematical analysis, calibration of the obtained data, displaying the calculated data in a readable format or plotting said data in a graphical form; and
f) Running a computer algorithm correlating the calculated data to either nitrogen concentration, boron concentration or plastic deformation in diamonds, thereby allowing grading of the diamond.

In a particular embodiment, the grading of the diamond comprises colour identification of said diamond based on the GIA colour scale, detection of plastic deformations in said diamond and determining whether said diamond is natural, treated or synthetic. In a further embodiment, the diamond may be polished or rough.

In a specific embodiment, the EM field which is applied to the diamond in the method of the present invention is the EM filed with a radiofrequency (RF) or terahertz frequency (THz) in a frequency domain range of up to 30 THz.

In some embodiments, the present invention describes a grading device for grading a diamond comprising:
a) an electromagnetic field (EM) generator configured to generate the EM field and apply said field to the to the diamond within the grading device;
b) a signal detector configured to record a modulated signal received from the diamond, after applying the EM field, in a form of S-parameters as a function of frequency or any other parameter, such as complex dielectric constant, complex magnetic permeability, capacitance, inductance, resistance, reflectance, absorbance, or any other quantity that can be deduced by applying the EM field and recording said signal, and transmit said signal to a computing unit; and
c) the computing unit configured to receive the signal from the signal detector, to convert said signal into computer data containing information about either the amplitude, or phase, or both of said the recorded S-parameters as a function of frequency or said any other parameter, to perform calculations relating to mathematical analysis and calibration of the data, to display said data in a readable format or to plot said data in a graphical form, and to run algorithm correlating the data with either nitrogen concentration, boron concentration or plastic deformation in diamonds, thereby allowing to grade the diamond.

In a particular embodiment, the grading device is designed to operate in a radiofrequency (RF) range and comprises:
a) a radiofrequency (RF) signal generator configured to generate a signal in a frequency range of 0 to 3 THz and output said signal to a transmitting antenna;
b) the transmitting antenna connected to said generator via an electric cable and configured to transmit said signal into a waveguide, cavity or resonator;
c) said waveguide designed to accommodate the diamond, to receive the signal from the transmitting antenna and to transmit said signal through the diamond to a receiving antenna;
d) the receiving antenna connected to an amplitude and frequency detector via an electric cable and configured to receive the signal from the waveguide;
e) the amplitude and frequency detector configured to detect the signal received from the receiving antenna and transmit said signal to a computing unit; and
f) the computing unit configured to receive the signal from the amplitude and frequency detector, to convert said signal into computer data containing information about the amplitude and phase of said signal, to perform calculations relating to mathematical analysis and calibration of the data, to display said data in a readable format or to plot said data in a graphical form, and to run algorithm correlating the data with either nitrogen concentration, boron concentration or plastic deformation in diamonds, thereby allowing to grade the diamond.

In a specific embodiment, the device of the present invention further comprises a closed resonator with a container for placing the diamond. In a certain embodiment, the device further comprises a quadrature (I/Q) demodulator.

In another particular embodiment, the grading device further comprises a capacitor and a capacitance-measuring unit, said unit connected to the capacitor and is capable of measuring a change in capacitance of the diamond, said change in capacitance is induced by the diamond placed inside said capacitor for grading, and said change is an indicator of nitrogen or boron concentration or of plastic deformation in the diamond crystal.

In another particular embodiment, the grading device further comprises an inductance coil and an inductance-measuring unit, said unit connected to the inductance coil and is capable of measuring a change in inductance of the diamond, said change in inductance is induced by the diamond placed inside said inductance coil for grading, and said change is an indicator of nitrogen or boron concentration or of plastic deformation in the diamond crystal.

Various embodiments may allow various benefits and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

Disclosed embodiments will be understood and appreciated more fully from the following detailed description taken in conjunction with the appended figures. The drawings included and described herein are schematic and are not limiting the scope of the disclosure. It is also noted that in the drawings, the size of some elements may be exaggerated and, therefore, not drawn to scale for illustrative purposes. The dimensions and the relative dimensions do not necessarily correspond to actual reductions to practice of the disclosure.

The patent or application file contains at least one drawing executed in color. Copies of this patent or patent application publication with color drawing(s) will be provided by the Office upon request and payment of the necessary fee.

DETAILED DESCRIPTION

Figure 1:
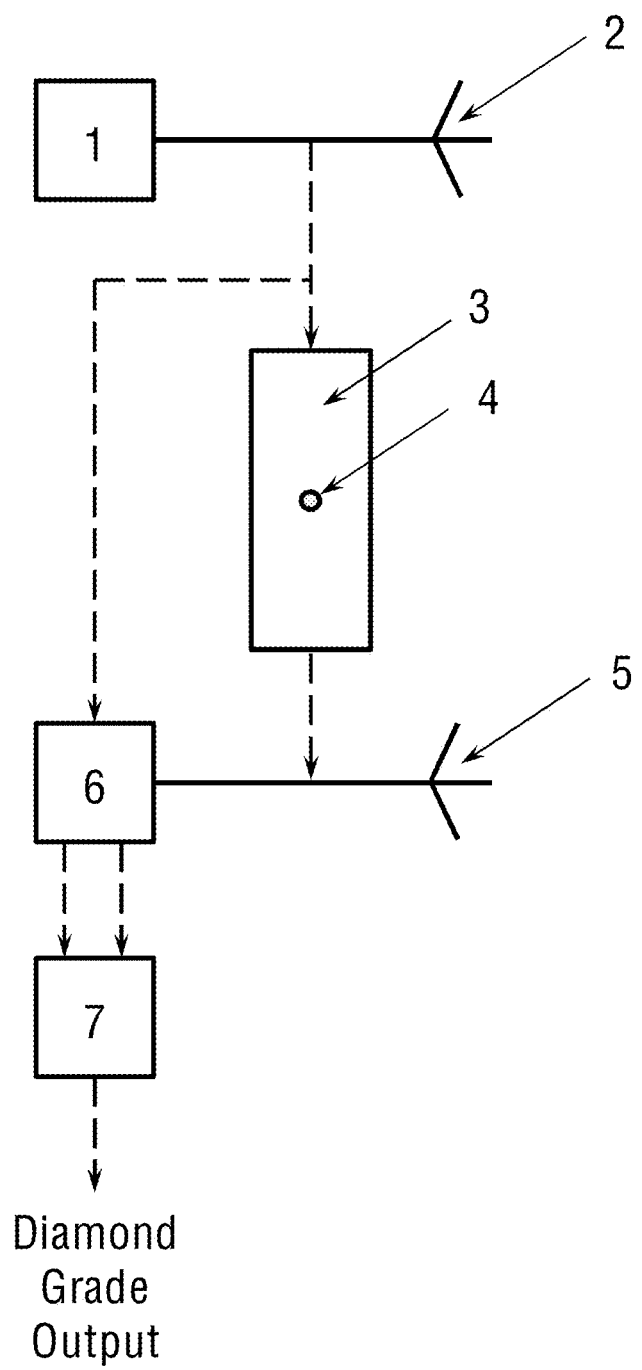
FIG. 1 schematically shows the device of the present embodiments for grading diamonds.

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, is "open ended" and means the elements recited, or their equivalent in structure or function, plus any other element or elements which are not recited. It should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising x and z" should not be limited to devices consisting only of components x and z. Also, the scope of the expression "a method comprising the steps x and z" should not be limited to methods consisting only of these steps.

Unless specifically stated, as used herein, the term "about" is understood as within a range of normal tolerance in the art, for example within two standard deviations of the mean. In one embodiment, the term "about" means within 10% of the reported numerical value of the number with which it is being used, preferably within 5% of the reported numerical value. For example, the term "about" can be immediately understood as within 10%, 9%, 8%, 7%, 6%, 5%, 4%, 3%, 2%, 1%, 0.5%, 0.1%, 0.05%, or 0.01% of the stated value. In other embodiments, the term "about" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges, for example from 1-3, from 2-4, and from 3-5, as well as 1, 2, 3, 4, 5, or 6, individually. This same principle applies to ranges reciting only one numerical value as a minimum or a maximum. Unless otherwise clear from context, all numerical values provided herein are modified by the term "about". Other similar terms, such as "substantially", "generally", "up to" and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value.

As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

In one aspect of the present invention, there is a method for grading a diamond comprising the steps of:
  a) Placing the diamond to be graded into a grading device;
  b) Applying an electromagnetic field (EM) to the diamond within the grading device;
  c) Recording a modulated signal received from the diamond, after applying the EM field in a form of S-parameters as a function of frequency or any other parameter, such as complex dielectric constant, complex magnetic permeability, capacitance, inductance, resistance, reflectance, absorbance, or any other parameter that can be deduced by applying said EM field;
  d) Processing the recorded signal in the processing unit to obtain data containing information about either an amplitude, or phase, or both of the recorded S-parameters as a function of frequency or said any other parameter;
  e) Performing calculations relating to mathematical analysis, calibration of the obtained data, displaying the calculated data in a readable format or plotting said data in a graphical form; and
  f) Running a computer algorithm correlating the calculated data to either nitrogen concentration, boron concentration or plastic deformation in diamonds, thereby allowing grading of the diamond.

In a specific embodiment, the method of the present invention for grading a diamond comprises:
  a) Placing the diamond to be graded into a grading device;
  b) Irradiating the diamond with the RF or THz signal in a frequency domain range of up to 30 THz;
  c) Recording a modulated signal received from the diamond after the irradiation in a form of S-parameters as a function of frequency or any other parameter, such as complex dielectric constant, complex magnetic permeability, capacitance, inductance, resistance, reflectance, absorbance, or any other quantity that can be deduced by irradiation of the diamond;
  d) Processing the recorded signal in the processing unit to obtain data containing information about either amplitude, or phase, or both of the recorded S-parameters as a function of frequency or said any other parameter;
  e) Performing calculations relating to mathematical analysis, calibration of the obtained data, displaying the calculated data in a readable format or plotting said data in a graphical form; and
  f) Running computer algorithm correlating the calculated data to either nitrogen concentration, boron concentration or plastic deformation in diamonds, thereby allowing grading of the diamond.

The term "grading" of diamonds according to the present embodiments is not limited only to their colour identification based on the GIA diamond colour scale but may also comprise identification of plastic deformations in diamonds and separation of treated and synthetic diamonds from their natural counterparts. Also, the diamonds graded by the method of the present embodiments may be either polished or rough.

In another aspect, the present invention describes a grading device for grading a diamond comprising:
  a) an electromagnetic field (EM) generator configured to generate the EM field and apply said field to the to the diamond within the grading device;
  b) a signal detector configured to record a modulated signal received from the diamond, after applying the EM field, in a form of S-parameters as a function of frequency or any other parameter, such as complex dielectric constant, complex magnetic permeability, capacitance, inductance, resistance, reflectance, absorbance, or any other quantity that can be deduced by applying the EM field and recording said signal, and transmit said signal to a computing unit; and
  c) the computing unit configured to receive the signal from the signal detector, to convert said signal into computer data containing information about either the amplitude, or phase, or both of said the recorded S-parameters as a function of frequency or said any other parameter, to perform calculations relating to mathematical analysis and calibration of the data, to display said data in a readable format or to plot said data in a graphical form, and to run algorithm correlating the data with either nitrogen concentration, boron concentration or plastic deformation in diamonds, thereby allowing to grade the diamond.

In a specific embodiment, the EM field which is applied to the diamond in the method of the present invention is the EM filed with a radiofrequency (RF) or terahertz frequency (THz) in a frequency domain range of up to 30 THz. In another embodiment, the device of the present invention further comprises a closed resonator with a container for placing the diamond.

As mentioned above, the present UV-Vis and IR instruments and methods are capable of correctly grading only about 70-85% of all the polished diamonds in the trade. The problem of incorrect grading of rough diamonds having reduced transparency is even worse. This results in downgrading of many diamonds and incurring significant losses in diamond deals. The problem is originated from the fact that low transparency of the rough diamonds creates considerable optical losses of the transmitted UV-Vis or IR light beam passing through the graded diamond crystals and makes the light propagation more diffusive than ballistic. The diffusive photons are clearly unwanted, because they create incoherent and diffusive background. Such resonant elastic scattering of light may be visualised as a chain of coherent absorption and re-emission events. Photons are then re-emitted in many random directions as the wave-vector is not conserved by the system. The resonant scattering results in the significant increase of the mean trajectory of photons travelling through the medium. As a result, light spends much longer time in the medium, so that the percentage of its absorbed energy strongly increases as compared to the ballistic propagation regime. This results in the incorrect grading of the diamond.

In view of the above explanation, it becomes clear that the losses of light intensity in the diamond's crystals are larger for shorter wavelengths instruments. This is simply because the shorter wavelength irradiation produces more diffusive photons in the condensed medium. The optical losses are directly proportional to $1/\lambda^4$, where 2 is the wavelength. Therefore, the IR instruments operating in the range of $\lambda=700$ nm to 1 mm clearly supersede the UV-Vis instruments operating in the range of $\lambda=250$-700 nm in their accuracy of grading diamonds. However, the IR and FTIR techniques are much more complicated, not many dealers are able to use it and their accuracy still leaves much to be desired.

The present invention is based on much longer wavelengths spectroscopies in the radiofrequency (RF) and terahertz (THz) range that do not suffer from any optical losses and from sensitivity to the exact shape of the diamond surface (the diamond crystal geometry). In fact, these low-energy spectroscopies are surprisingly found to be only sensitive to dielectric properties of the diamond crystals. Since nitrogen and boron have their specific magnetic and electric properties, which modify the dielectric and/or magnetic permeability of the diamond, the transmitted RF or THz signal or other responses to electromagnetic signals are indicative of the dielectric content of the diamond crystals.

In general, the RF and terahertz THz radiation are shown to be very important in many technological fields because of the unique capability of these low energy electromagnetic waves to interact with vibrations of atoms within molecules and crystals. The RF and THz spectroscopies use wavelengths beyond those traditionally used for molecular and crystal analysis. Various materials have found to be active in the frequency range up to 30 THz. These frequency domains and the spectral range between the upper end of the radio frequencies and the lowest optical frequencies are named the 'Terahertz Gap', because so little was known about them and because of the absence of radiation sources and detectors.

Low energy RF and THz vibrational spectroscopies are based on the interaction of the RF or THz radiation with internal molecular vibrations of low energy. Because of their small size and relatively low absorption coefficient, the waves of the RF and THz radiation easily propagate through the entire molecular object, such as a diamond crystal. The width of individual spectral lines and the intensity of resonance features, which are observed in the RF and THz spectroscopies, are extremely sensitive to the relaxation processes of atomic dynamics (displacements) within the crystal. Those relaxation processes determine the discriminative capabilities of the spectroscopy. Appropriate spectral resolution must be used in the RF and THz spectroscopies to be able to acquire qualitative as well as quantitative information used to identify certain parameters of crystals that will, in turn, increase detection accuracy and selectivity.

Reference is now made to FIG. 1 schematically showing an exemplary device, which is used in the method of the present embodiments for grading diamonds. The device is configured to generate a signal in a frequency range of 0 to 30 THz, which includes the microwave range (300 MHz to 30 GHz), the millimetre wave range (30 GHz to 300 GHz) and terahertz range (300 GHz to 30 THz). Operating at such long wavelengths, the device is essentially free of any optical losses and from sensitivity to the diamond surface geometry, as explained above. The device is calibrated for determining the concentration of nitrogen in a diamond crystal lattice and consequently determines the colour of the diamond.

The exemplary device of the present invention comprises the following components:
a) an RF generator (1) configured to generate an RF signal in a frequency range of 0 to 3 THz and output said signal to a transmitting antenna (2);
b) the transmitting antenna (2) connected to said generator (1) via an electric cable and configured to transmit said signal into a waveguide (3);
c) the waveguide (3) designed to accommodate a diamond (4), to receive the signal from the transmitting antenna (2) and to transmit said signal through the diamond (4) to a receiving antenna (5);
d) the receiving antenna (5) connected to an amplitude and frequency detector (6) via an electric cable and configured to receive the signal from the waveguide (3);
e) the amplitude and frequency detector (6) configured to detect the signal received from the receiving antenna (5) and transmit said signal to a computing unit (7); and
f) the computing unit (7) configured to receive the signal from the amplitude and frequency detector (6), to convert said signal into computer data containing information about the amplitude and phase of said signal, to perform calculations relating to mathematical analysis and calibration of the data, to display said data in a readable format or to plot said data in a graphical form, and to run algorithm correlating the data with the nitrogen concentration, thereby allowing to grade the diamond.

In a particular embodiment, the RF generator (1), the amplitude and frequency detector (6) and a computing unit (7) are the component units of a network analyser, which is a device capable of measuring various parameters of electric circuits or networks. The commonly measured parameters by network analysers are S-parameters (scattering parameters) or the elements of an S-matrix (scattering matrix), which describe electrical behaviour of electrical networks when undergoing various steady state stimuli by electrical signals. The S-parameters numerically (in dB) characterise a signal between various ports of the network analysers. Most network analysers have two test ports permitting measurement of four S-parameters between these ports ($S_{11}$, $S_{12}$, $S_{21}$ and $S_{22}$). As in the present configuration, the basic architecture of a network analyser involves the frequency sweep signal generator (1), a test set, which is the waveguide (3) with the diamond (4), and the computing unit (7) or processor optionally equipped with a display. In some setups, these units may be distinct instruments. The network analyser used in examples of the present application was a Keysight PNA network analyser. After calibration of the device and finding one single RF frequency at which the effect of the nitrogen concentration on attenuation of the transmitted signal in diamonds crystals is most pronounced, the grading of diamonds could be performed only at this particular frequency.

In a further embodiment, the generated RF signal may be either a sweeping sine waveform signal or a signal at a single RF frequency, at which the effects of the nitrogen or boron concentration, or plastic deformations in diamonds crystals on the attenuation of the transmitted signal are most pronounced.

Figure 2:
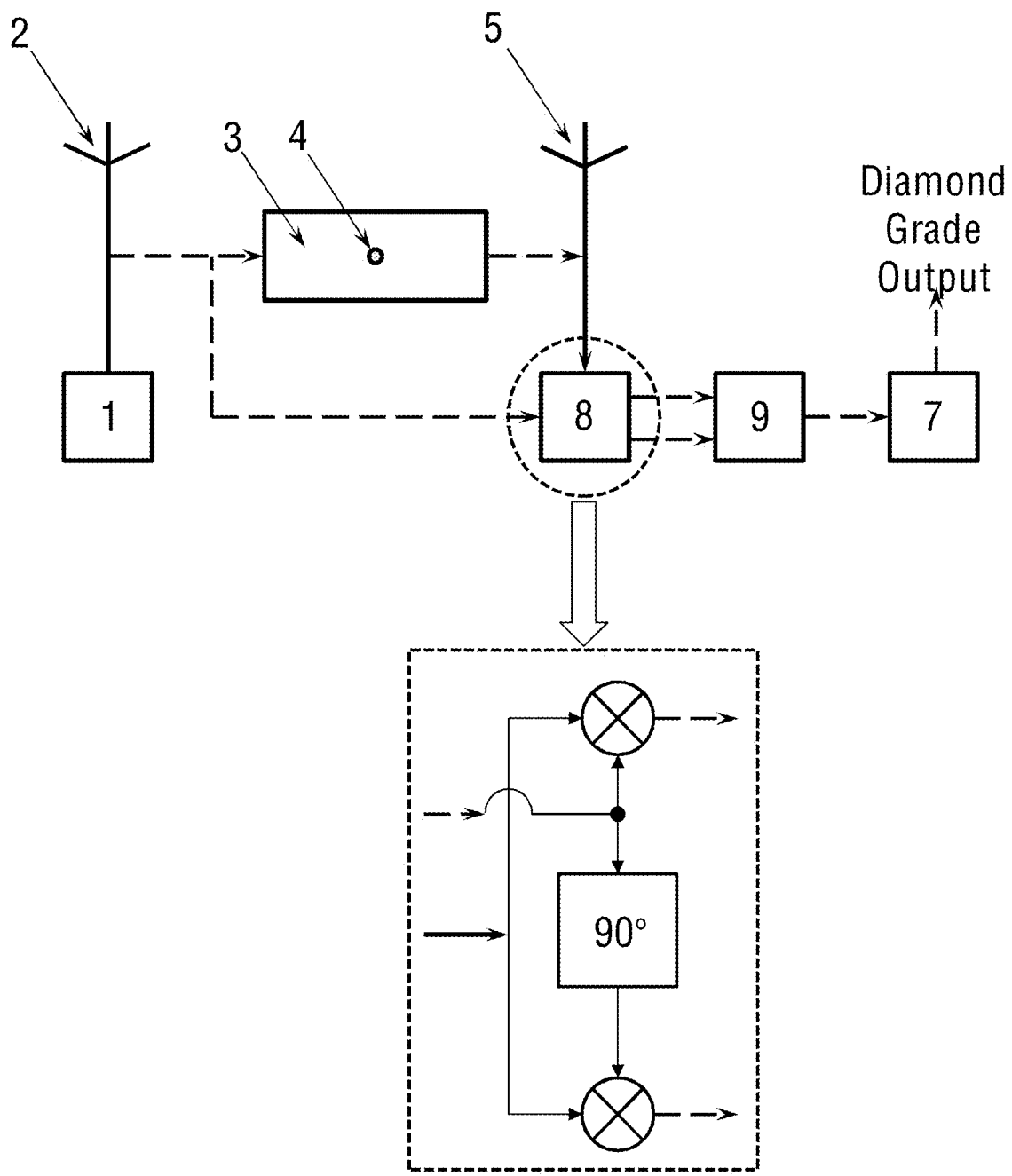
FIG. 2 schematically shows the device of the present embodiments with I/Q demodulator for grading diamonds.

In another embodiment, the device of the present invention further comprises a quadrature (I/Q) demodulator. An exemplary I/Q demodulator used in the present invention is Analog Devices I/Q demodulator of the ADL 538x series. As schematically shown in FIG. 2, the I/Q demodulator (8) is installed between the waveguide (3) and the amplitude and phase detector (9).

The operation of the I/Q demodulator (8) can be explained by representing its radiofrequency input signal $S_{RF}$(t) as a combination of two double sideband modulated quadrature carriers:

$$S_{RF}(t)=S_I(t)+S_Q(t)=I(t)\cos \omega_{RF}t-Q(t)\sin \omega_{RF}t \quad (1)$$

Figure 3A:
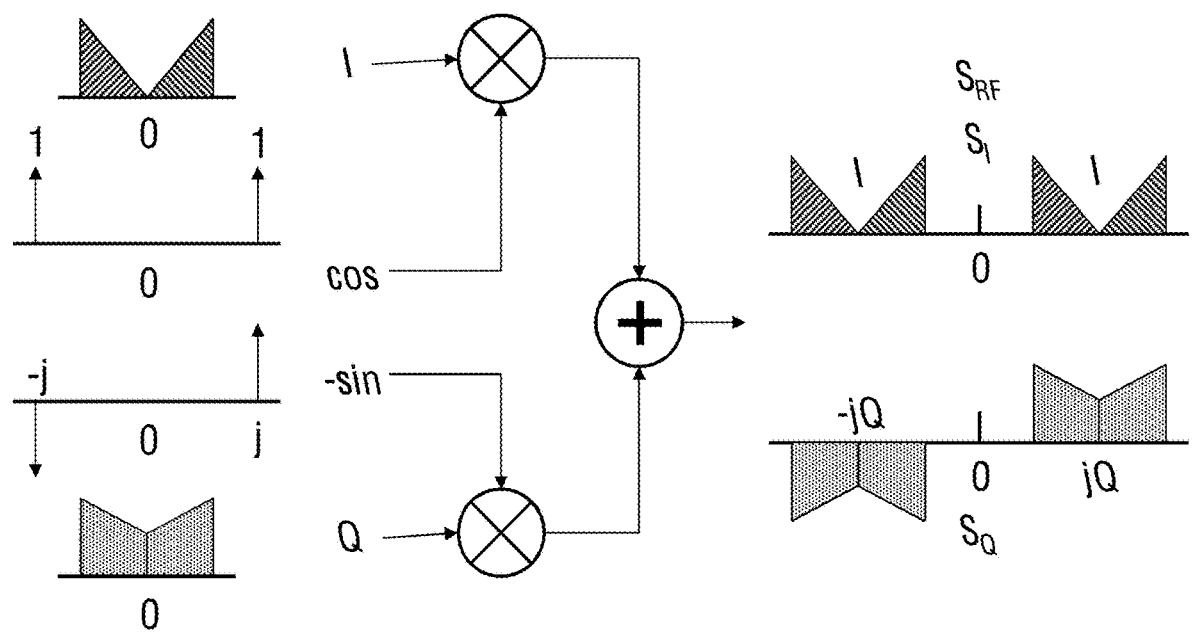
FIG. 3a schematically represents the concept of I/Q modulation.
Figure 3B:
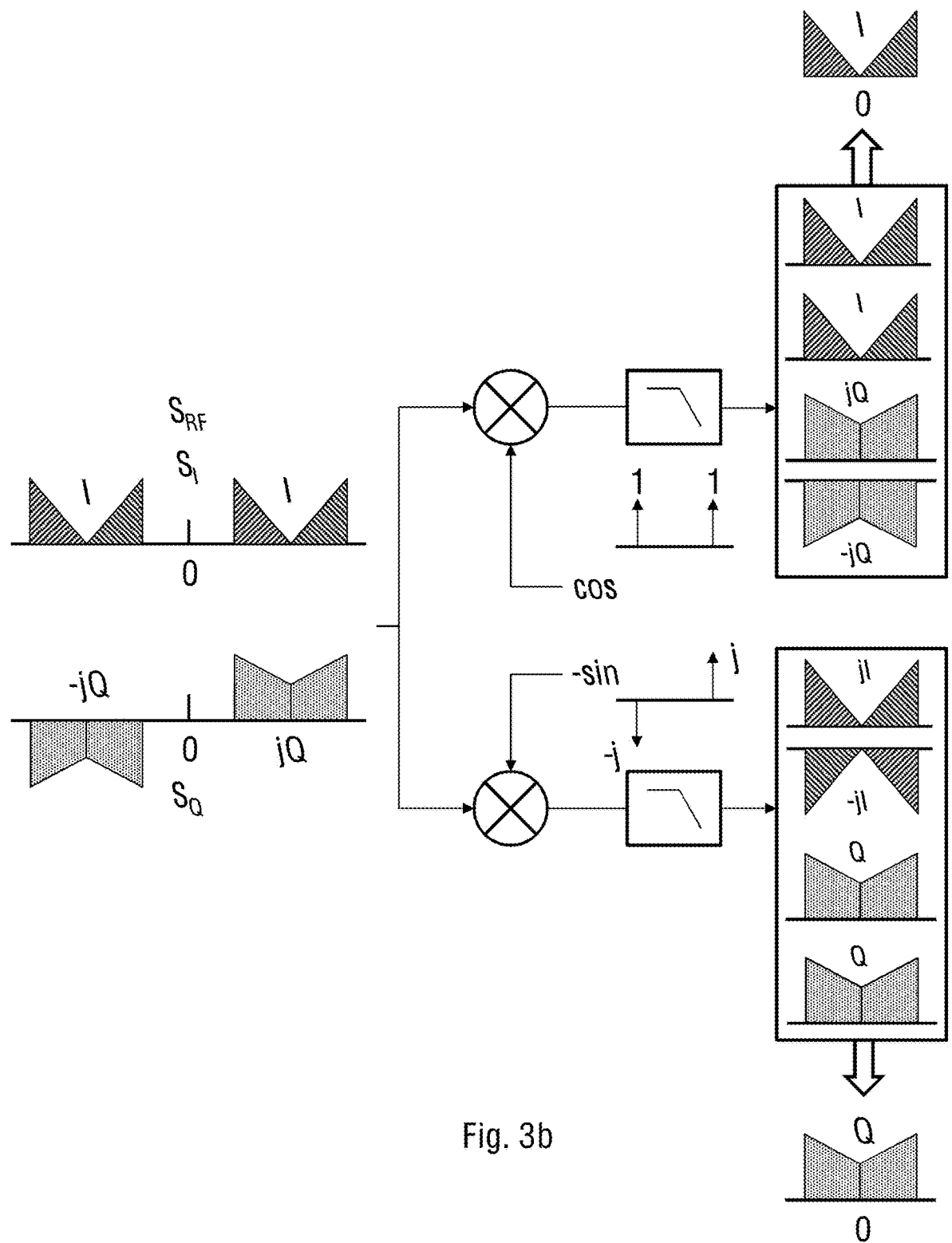
FIG. 3b schematically represents the concept of I/Q demodulation.
Figure 4A:
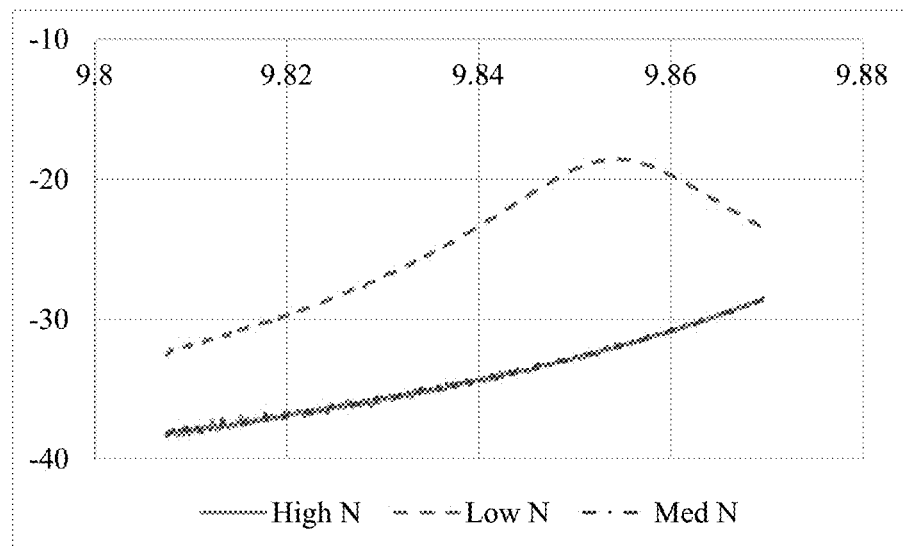
FIG. 4a shows the experimental $S_{12}$ amplitude measured with the closed resonator device of the embodiments for three different diamonds at 9.8 GHz frequency.
Figure 4B:
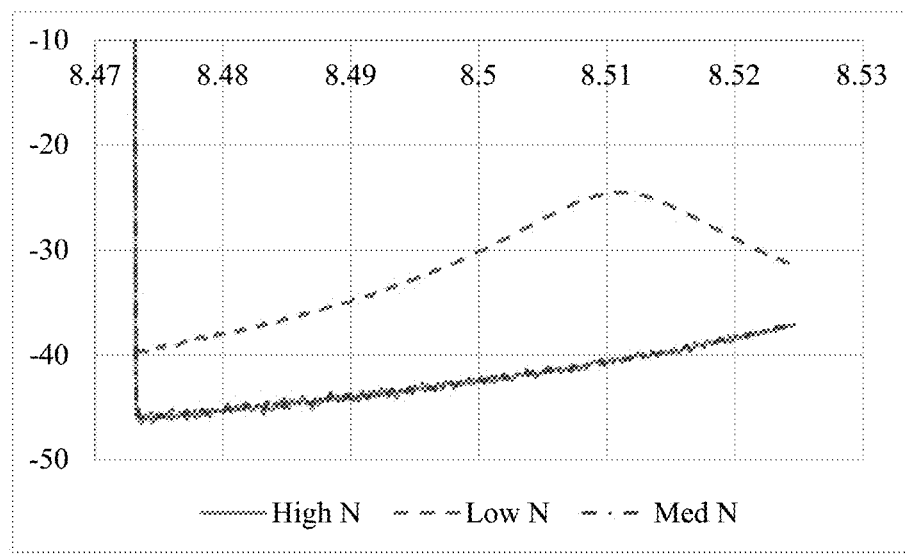
FIG. 4b shows the experimental $S_{12}$ amplitude measured with the closed resonator device of the embodiments for three different diamonds at 8.4 GHz frequency.
Figure 4C:
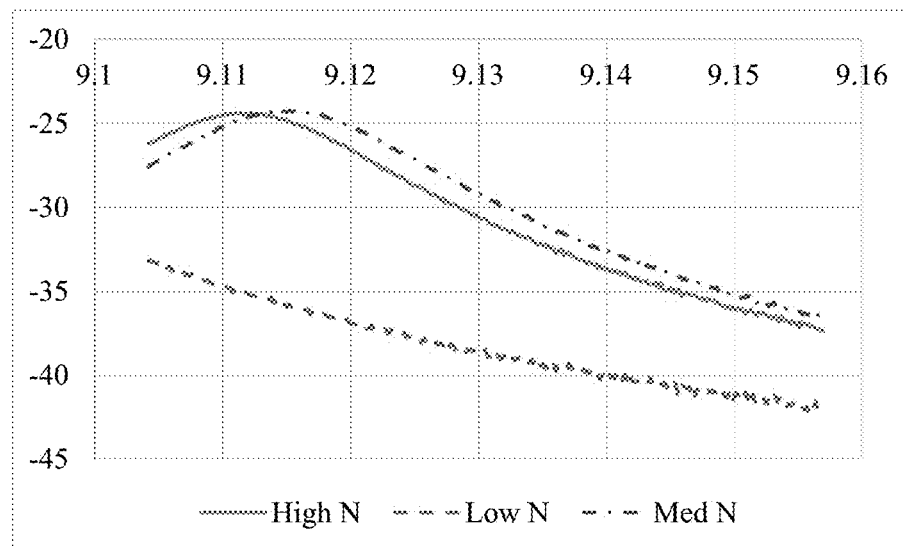
FIG. 4c shows the experimental $S_{12}$ amplitude measured with the closed resonator device of the embodiments for three different diamonds at 9.13 GHz frequency.
Figure 4D:
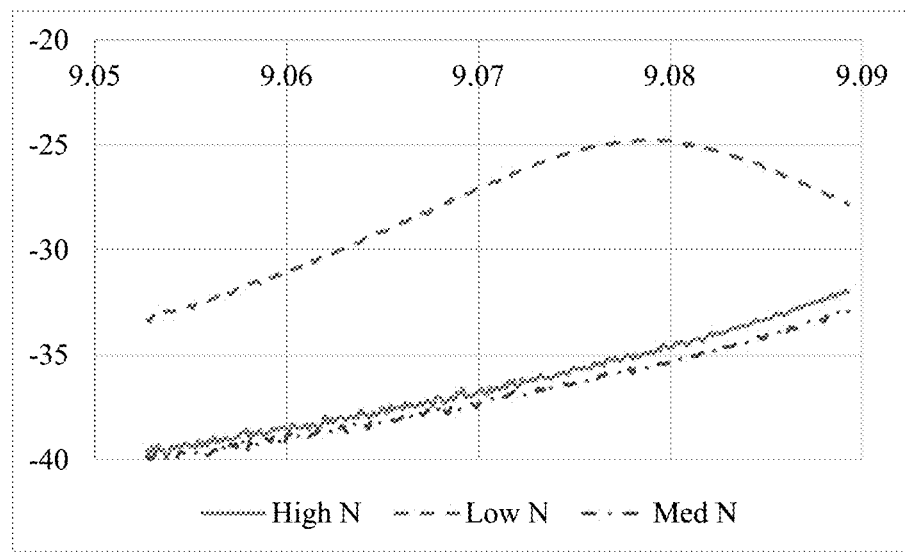
FIG. 4d shows the experimental $S_{12}$ amplitude measured with the closed resonator device of the embodiments for three different diamonds at 9.0 GHz frequency.
Figure 4E:
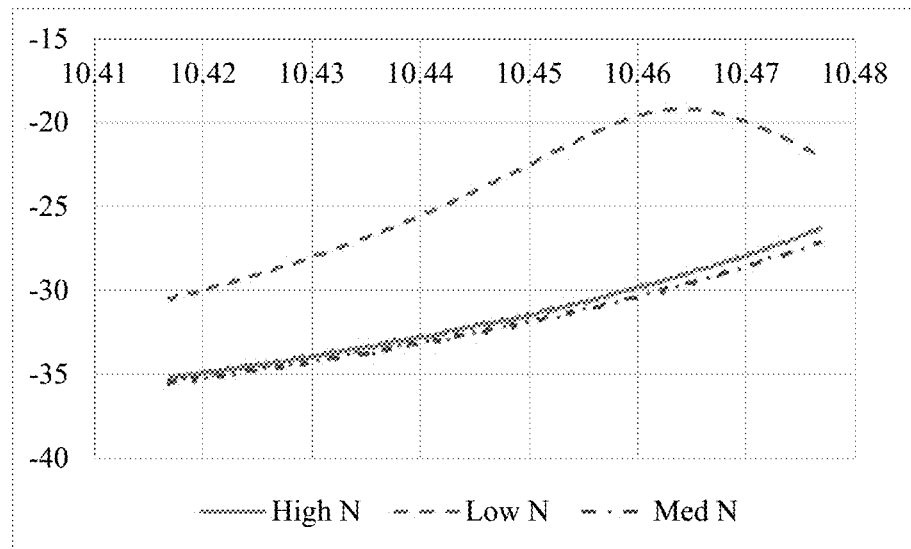
FIG. 4e shows the experimental $S_{12}$ amplitude measured with the closed resonator device of the embodiments for three different diamonds at 10.4 GHz frequency.
Figure 4F:
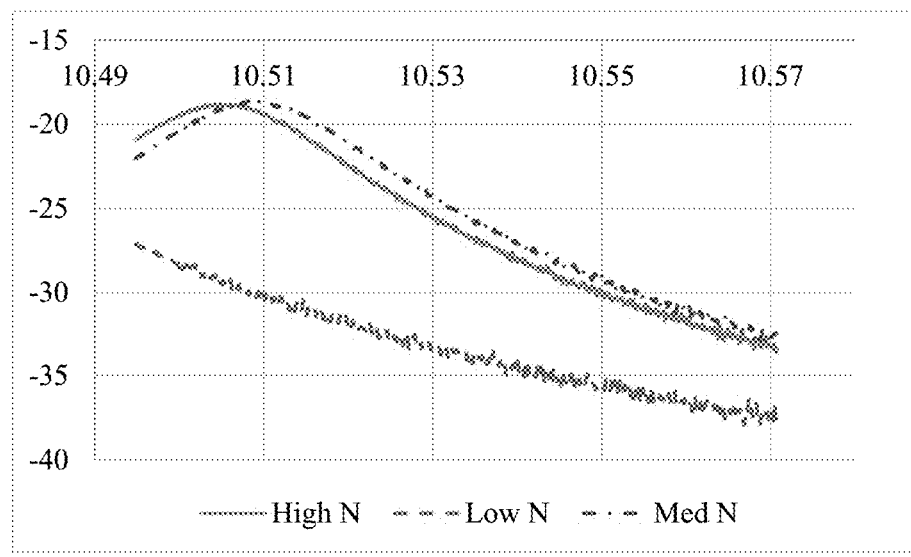
FIG. 4f shows the experimental $S_{12}$ amplitude measured with the closed resonator device of the embodiments for three different diamonds at 10.5 GHz frequency.
Figure 4G:
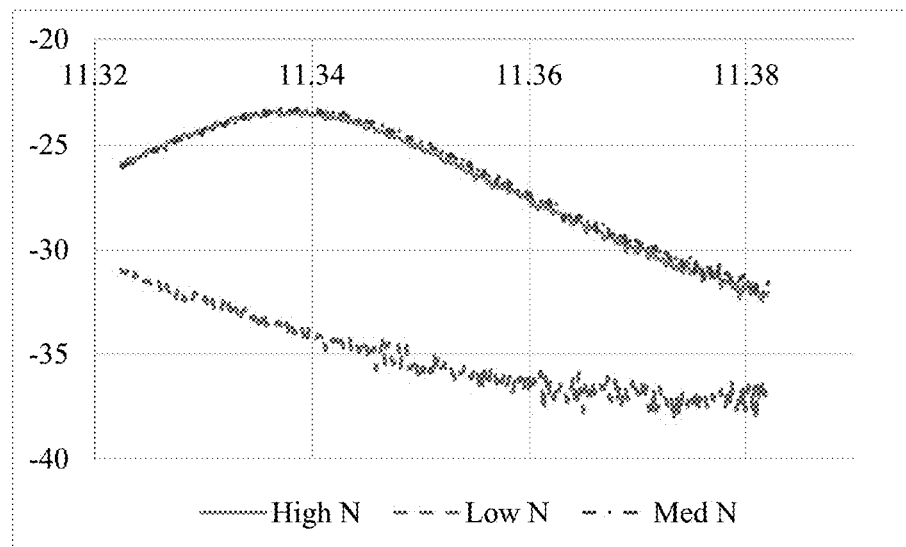
FIG. 4g shows the experimental $S_{12}$ amplitude measured with the closed resonator device of the embodiments for three different diamonds at 11.3 GHz frequency.
Figure 4H:
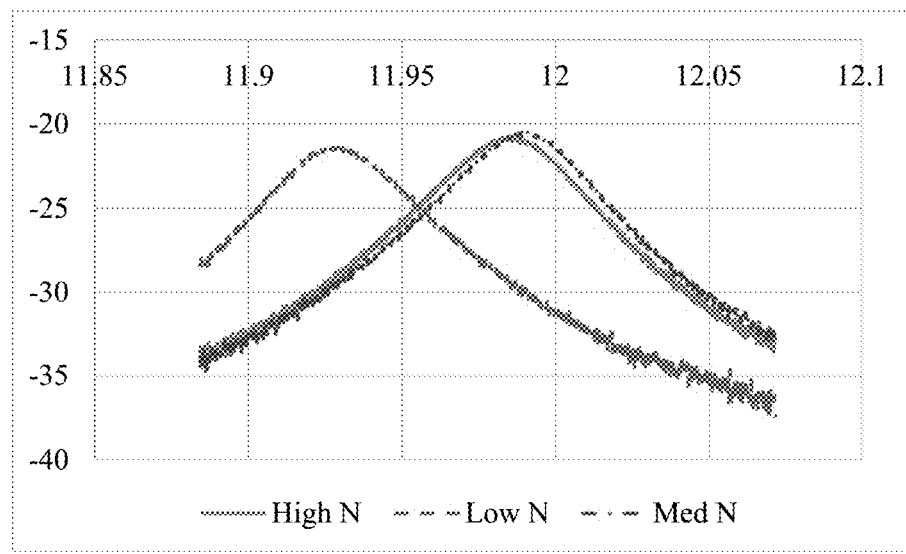
FIG. 4h shows the experimental $S_{12}$ amplitude measured with the closed resonator device of the embodiments for three different diamonds at 11.9 GHz frequency.
Figure 5A:
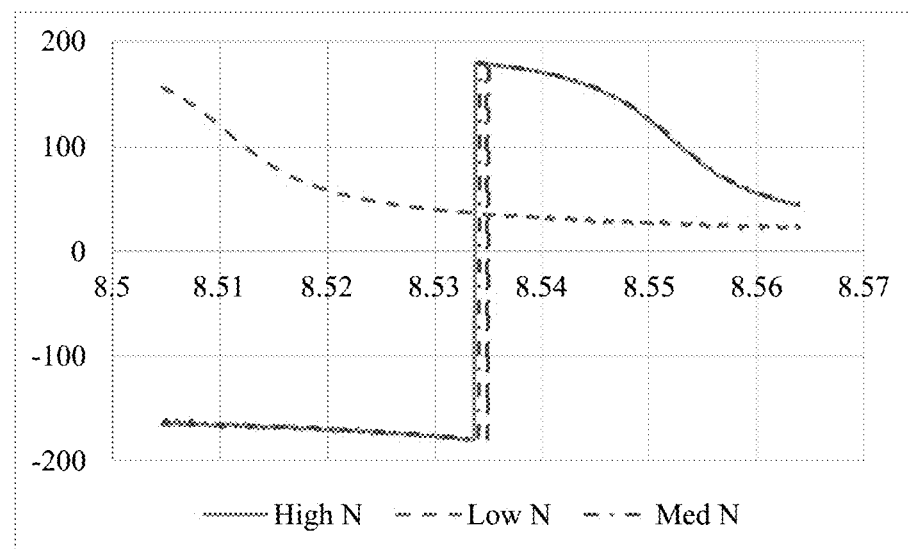
FIG. 5a shows the experimental $S_{12}$ phase measured with the closed resonator device of the embodiments for three different diamonds at 8.5 GHz frequency.
Figure 5B:
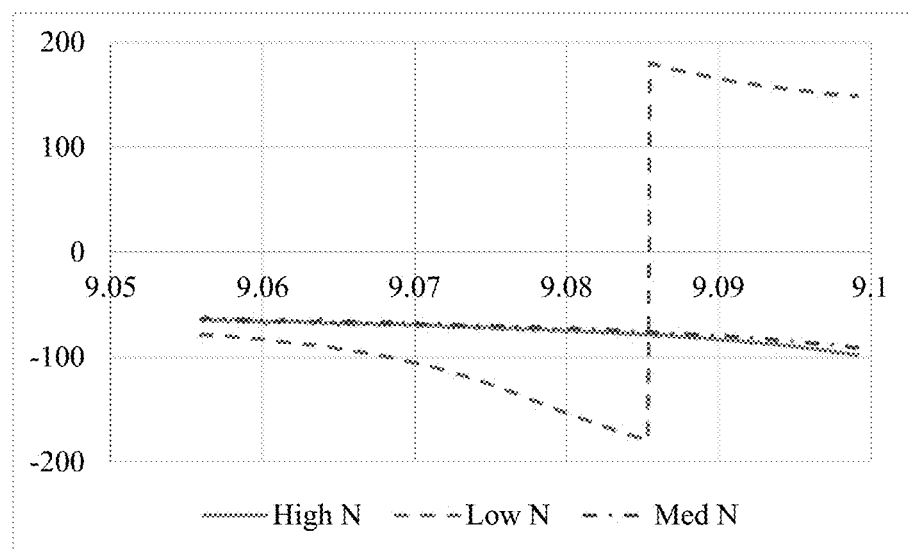
FIG. 5b shows the experimental $S_{12}$ phase measured with the closed resonator device of the embodiments for three different diamonds at 9.0 GHz frequency.
Figure 5C:
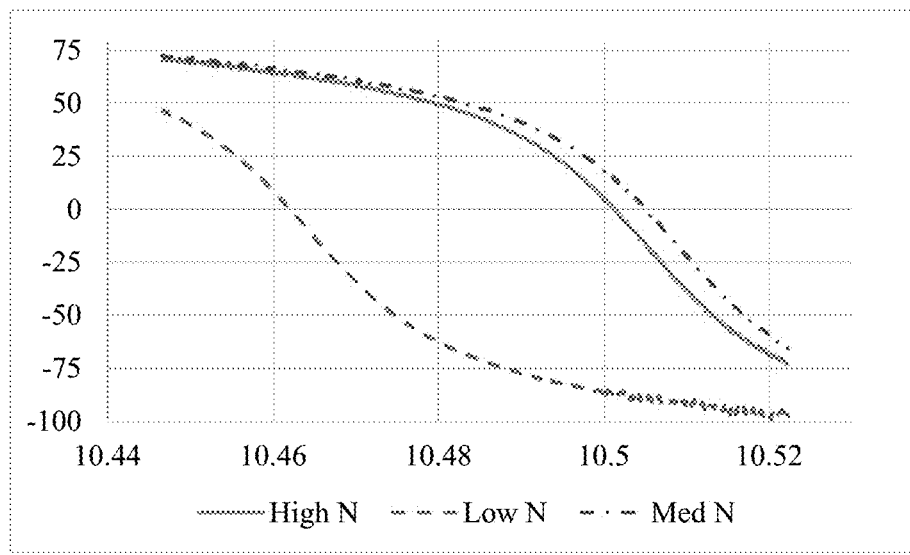
FIG. 5c shows the experimental $S_{12}$ phase measured with the closed resonator device of the embodiments for three different diamonds at 10.4 GHz frequency.
Figure 5D:
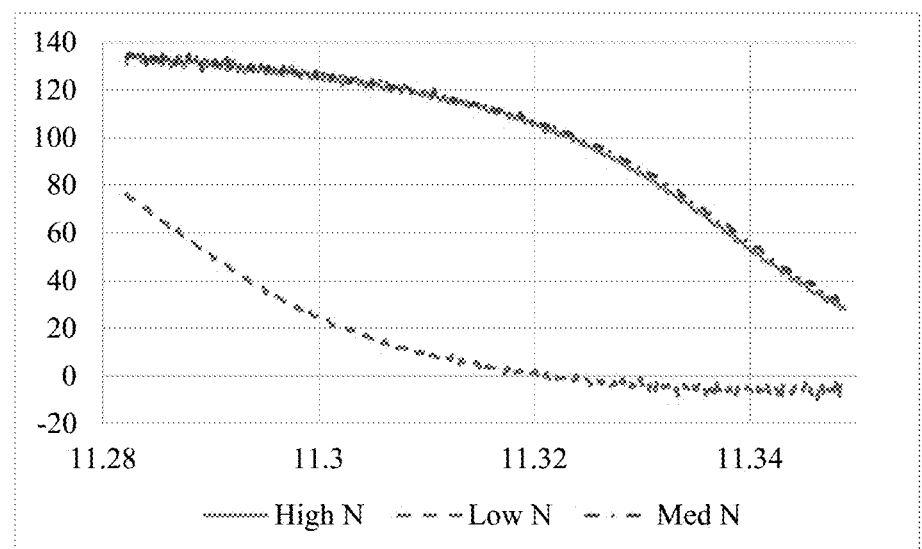
FIG. 5d shows the experimental $S_{12}$ phase measured with the closed resonator device of the embodiments for three different diamonds at 11.3 GHz frequency.

As shown in FIG. 3a, the in-phase component I(t) and quadrature component Q (t) are baseband signals that can be viewed as inputs to an ideal I/Q modulator generating the signal $S_{RF}$ (t). As shown in FIG. 3b, the I/Q demodulator achieves perfect reconstruction of I(t) and Q (t) by exploiting the quadrature phase relation between $S_I$(t) and $S_Q$(t).

The frequency-domain representation of a −90° phase shift corresponds to multiplication by the Hilbert transform:

$$H(j\omega)=-j \, \text{sgn}(\omega) \quad (2)$$

It converts a spectrum with even symmetry around $\omega=0$ to a spectrum with odd symmetry and vice versa. The spectra of $S_I$(t) and $S_Q$(t) thus exhibit different symmetry, where $S_I$(t) has even symmetry and $S_Q$(t) has odd symmetry. Down conversion of the even RF input component $S_I$(t) with the even LO (cosine) retrieves I(t), while $S_Q$(t) with the odd LO (sine) retrieves Q(t). Cross-combinations of even and odd yield zero. An error $\varphi$ on the quadrature relation between the LO outputs causes crosstalk between the I- and Q-channels. Using the I-phase channel as reference, an even component is then introduced in the Q-channel LO:

$$\sin(\omega_{RF}t+\varphi)=\sin(\omega_{RF}t)\cos \varphi+\cos(\omega_{RF}t)\sin \varphi \quad (3)$$

As a result, a contribution of I(t) to the Q-channel output $Q_{out}$(t) is:

$$Q_{out}(t)=Q(t)\cos \varphi+I(t)\sin \varphi \quad (4)$$

Thus, the I/Q demodulator (8) is designed to create and combine quadrature phase components of the input signals. The exemplary I/Q demodulator (8) used in the present invention is Analog Devices RF/IF gain and phase detector chip AD8302. It is connected and outputs the signal to the amplitude and phase detector (9), which performs the amplitude measurement in order to measure phase difference between the received signals. The AD8302 chip provides a simple way to measure amplitude log ratio and the phase difference of two signals simultaneously. Phase detection is done at the carrier frequency, hence, it can be used in a long-wavelength phase locked loop (PLL) or delay locked loop (DLL) to reduce power consumption by eliminating frequency dividers required in different approaches. K. H. Hu et al in "*Simple Amplitude and Phase Detector for Accelerator Instrumentation*", AIP Conference Proceedings (2002), 648, pp. 523-530 (the 10th Beam Instrumentation Workshop held 6-9 May, 2002 in Upton, New York; edited by G. A. Smith and T. Russo. New York: American Institute of Physics), provide more details on this AD8302 chip and its operation.

The waveguide (3) is a signal transmission component consisting of a hollow, metal tube, for example aluminium. The tube wall provides distributed inductance, while the empty space between the tube walls provides distributed capacitance. This waveguide acts as an electrical transmission line and is much simpler than a two-conductor cable, especially a coaxial cable, in its manufacture and maintenance. With only a single conductor, which is actually the waveguide's wall, there are no concerns with proper conductor-to-conductor spacing, or of the consistency of the dielectric material, since the only dielectric in a waveguide is air. Also, moisture is not a problem in such waveguide either, and so it is often spared the necessity of any filling.

The waveguide (3) may be thought of as a conduit for electromagnetic energy directing the signal rather than conducting it. In a sense, it directs the high-frequency sine waves as the banks of a river direct a tidal wave. However, because waveguides are single-conductor elements, the propagation of electrical energy down a waveguide is of a very different nature than the propagation of electrical energy down a two-conductor transmission line. In general, such waveguides transmit the generated waveform signals in a higher frequency range and at much lower loss than coaxial cables. The waveguides are practical only for signals of such high frequency, where the wavelength approaches the cross-sectional dimensions of the waveguide.

The transmitting antenna (2) and the receiving antenna (5) are small antenna-like coupling devices attached to or inserted into the waveguide (3) creating a closed configuration of the device. Alternatively, they may be positioned at the opposite edges of the waveguide creating an open configuration of the device. The transmitting antenna (2) is responsible for sending the signal to the diamond placed in the waveguide, whereas the receiving antenna (5) is responsible for receiving the signal passed through the diamond. These antennas may take the form of a dipole, for example, wherein two open-ended stub wires have appropriate length. Alternatively, these antennas may take the form of a half-dipole, for example, wherein a single stub is similar in principle to a "whip" antenna, ¼×λ in physical length. Also, these antennas may constitute a short loop of wire terminated on the inside surface of the waveguide.

In a particular embodiment, the waveguide in the device of the present embodiments may be replaced with a closed resonator, which is an oscillating device exhibiting resonant behaviour at certain resonant frequencies with greater amplitude than at others. The closed resonator contains a small container for placing a graded diamond and is capable of generating waves of specific frequencies.

In a further specific embodiment, the grading device further comprises a capacitor and a capacitance-measuring unit, said unit connected to the capacitor and is capable of measuring a change in capacitance of the diamond, said change in capacitance is induced by the diamond placed inside said capacitor for grading, and said change is an indicator of nitrogen or boron concentration or of plastic deformation in the diamond crystal.

In another particular embodiment, the grading device further comprises an inductance coil and an inductance-measuring unit, said unit connected to the inductance coil and is capable of measuring a change in inductance of the diamond, said change in inductance is induced by the diamond placed inside said inductance coil for grading, and said change is an indicator of nitrogen or boron concentration or of plastic deformation in the diamond crystal.

In the following experimental section, initial measurements of the dielectric properties of a series of master diamonds in the D, E, F, H and L colour ranges, having the average size of 0.30 carats, clearly demonstrated that the absorbed signal is affected by nitrogen concentration in the diamond. These diamonds have been characterised and colour graded by the GIA (Gemmological Institute of America) and further used for calibration of the device.

It is very important to calibrate the device of the present embodiments before or during its operation. The "calibration sample" is a term used herein to define a sample diamond where the diamond or diamonds to be graded or identified are known diamonds having known nitrogen concentration used for calibrating the hardware of the device or acquired data. The calibration sample is used when a calibration method is employed.

One of the calibration methods is known as an adaptive calibration, in which parameters are changed during the measurement process in order to minimize errors. An exemplary, but non-limiting, method that may be used is the well-known least mean squares filter method. In the present application, measurement errors may be estimated by measuring the difference between the expected results of the calibration sample(s) to the actual measured results of the calibration sample(s). The obtained differences are measured in the two-dimensional space of phase and amplitude. Each of the measured results of the sample diamonds is modified according to the calibration parameters in both dimensions of phase and amplitude. The modified measured results are then used to generate the calibration plot for the nitrogen concentration in a diamond crystal lattice of the samples which is used for identification or grading of the diamonds.

EXAMPLES

A preliminary study was carried out and included a series of experiments to find correlation between the chemical content of diamonds and their electro-magnetic properties. Electromagnetic characterisation included an amplitude and phase test for the entire spectrum in the range of 8 to 12.5 GHz, as well as the location of their free-spectral range in this frequency range and a test for an additional parameter is the group delay.

The following experiments were performed to examine the effect of nitrogen concentration:
(1) Three system configurations were examined: empty waveguide, waveguide with a diamond-free container and a waveguide with a diamond to test whether it has an electro-magnetic effect.
(2) To test the system's feasibility in diamond testing, 12 diamonds were tested with different properties and a number of parameters (diamond size, nitrogen concentration and nitrogen type).
(3) Three diamonds with similar weights and different nitrogen concentrations were tested to determine whether there was an electromagnetic change between the different nitrogen concentrations.
(4) Peak changes on measurements with different diamonds and different compositions were examined.
(5) The effect of the shape of the diamond in the container was examined, and it was found that the shape did not significantly affect the shift of the peaks.
(6) Stones of the same weight were tested with different nitrogen concentrations to test whether there is a correlation of the peaks location with the chemical composition.
(7) A linear relationship was found between the group delay and a particular form of nitrogen in a diamond crystal lattice.

Description of the Test Device

Diamonds were chosen of various sizes around 3.5 mm in diameter and 4 mm in height. The test device of the present embodiments with the following parameters was used for grading diamonds:

Keysight PNA Network Analyser.

Waveguide or closed resonator suitable for frequencies 8 GHz to 12.5 GHz and having dimensions of 0.4 to 0.9 inches.

A container printed with a three-dimensional printer at half the height of the waveguide and with the dimensions suitable for the waveguide and having a tab for release of a sample in experiments.

Coaxial-to-wave guide connectors at each side of the waveguide or closed resonator were used to connect the waveguide with the cables to the ports of the network analyser.

Experiment 1—Diamond Type

Three diamonds with different nitrogen concentration were examined:

Sample 2: A natural diamond weighing 0.27 carats with high nitrogen concentration of Type Ia, which was colourless.

Sample 3: A natural diamond weighing 0.28 carat with very low nitrogen concentration of Type IIa, which was HTPT-treated with 28,000 atm and 2,500° C. for 20 seconds, resulting in the yellow colour.

Sample 4: A natural diamond weighing 0.22 carats with medium nitrogen concentration of Type Ia containing Type Ib paramagnetic centres, which was HTPT-treated with 28,000 atm and 2,500° C. for 20 seconds, resulting in the brown-orange colour.

The following measurements with the three diamonds were conducted:

Measurement of the waveguide when it is empty.

Measurement of the waveguide with the container inside.

Measurement of the waveguide with the container and the Sample 2 diamond inside.

Measurement of the waveguide with the container and the Sample 3 diamond inside.

Measurement of the waveguide with the container and the Sample 4 diamond inside.

The above experiments allowed to determine whether there is a difference in the measurements and to conclude whether the observed change in the S-parameters resulted from the addition of the diamond to the waveguide. Moreover, it was made possible to compare the obtained results between different diamond samples containing different nitrogen concentrations and to receive an initial indication whether there is an effect on the electrical properties. To make a comparison with a closed resonator device, the same experiments with the same three diamonds, but with the closed resonator instead of the waveguide were performed. In the resonator experiments, appropriate mirrors were added to the edges of the waveguide. For each experiment, the tested device was calibrated. A frequency scan of all frequencies suitable for the waveguides was performed. Maximum resolution of 32,000 test points was obtained. The transmission power was −10 dBm. For each configuration, each of the dispersion matrix parameters was examined.

The S-matrix describes the return and transmission parameters for a network. In general and in the present experiments, the network has two inputs:

The S-matrix is given by the following:

$$\begin{pmatrix} b_1 \\ b_2 \end{pmatrix} = \begin{pmatrix} S_{11} & S_{12} \\ S_{21} & S_{22} \end{pmatrix} \begin{pmatrix} a_1 \\ a_2 \end{pmatrix}$$

Then $b_1 = S_{11}a_1 + S_{12}a_2$ and $b_2 = S_{21}a_1 + S_{22}a_2$, where $S_{11}$ defines the reflection, or what was received at port 1 of the network analyser when the transmission began at port 1;

$S_{12}$ defines how much of the transmission went from port 1 to port 2 of the network analyser;

$S_{21}$ defines how much of the transmission went from port 2 to port 1 of the network analyser; and $S_{22}$ defines the reflection, or what was received at port 2 of the network analyser when the transmission began at port 2.

For each measurement, one point of experimentally measured frequency with amplitude (dB) and phase (DEG) was obtained. For $S_{12}$ and $S_{21}$, a functional diagram was built. This diagram shows the amplitude function which is different for each of the graded diamonds. Differences around certain frequencies were measured in the second round of experiments.

In the experiments with the closed resonator configuration of the device, in the following frequencies, significant changes were detected between the diamonds having high and medium nitrogen concentration (Type I) and the diamond having low nitrogen concentration (Type II). The $S_{12}$ amplitude graphs shown in FIGS. 4a-4h along with the $S_{12}$ phase graphs shown in FIGS. 5a-5d clearly demonstrate that there is no significant difference between the diamonds of the same type.

| | Average $S_{12}$ amplitude, dB | |
|---|---|---|
| Frequency, GHz | Diamonds with high or medium nitrogen concentration | Diamonds with low nitrogen concentration |
| 8.48-8.52 | −41 | −31 |
| 9.05-9.085 | −38 | −28 |
| 9.10-9.15 | −28 | −38 |
| 9.80-9.87 | −35 | −25 |
| 9.90-9.95 | −25 | −33 |
| 10.42-10.47 | −32 | −22 |
| 10.50-10.57 | −25 | −35 |
| 11.24-11.30 | −35 | −25 |
| 11.33-11.38 | −25 | −35 |
| 11.90-11.95 | −32 | −22 |
| 11.95-12.05 | −25 | −35 |

The following conclusions were made from this experiment:

There are differences in the obtained amplitudes for the measurements with a diamond and without the diamond of diamond and diamond measurements in the inserted losses. Therefore, it is possible to identify the presence or absence of the diamond in the waveguide.

There are differences in phases in the transmission parameters $S_{12}$ and $S_{21}$, and therefore, it is possible to identify whether the diamond is present or absent in the waveguide also according to these parameters.

Similar changes in the parameters $S_{12}$ and $S_{21}$ were found in the experiments with the closed resonator.

There are differences around specific frequencies in which a significant change in both phase and amplitude between the diamonds having high or moderate nitrogen concentration can be seen compared to the diamond with low nitrogen concentration.

Experiment 2—Diamond Size

In order to confirm the hypotheses and in order to obtain maximum resolution, the second experiment was focused on two main peaks between 9.5 to 11.5 GHz. In this experiment the effect of the diamond size on the peak location was examined. The same device of the present embodiments was used in all the measurements. The following nitrogen-free diamonds of Type IIa were measured in this experiment:

Sample H4: Natural diamond weighing 0.14 carats.

Sample H2: Natural diamond weighing 0.38 carats.

Sample H3: Natural diamond weighing 0.56 carats.

For each measurement, one point of experimentally measured frequency with amplitude (dB) and phase (DEG) was obtained. For $S_{12}$ and $S_{21}$, a functional diagram was built. This diagram shows the amplitude function which is different for each of the tested configurations (the empty container and the diamonds H2, H3 and H4 inside the container).

Figure 6:
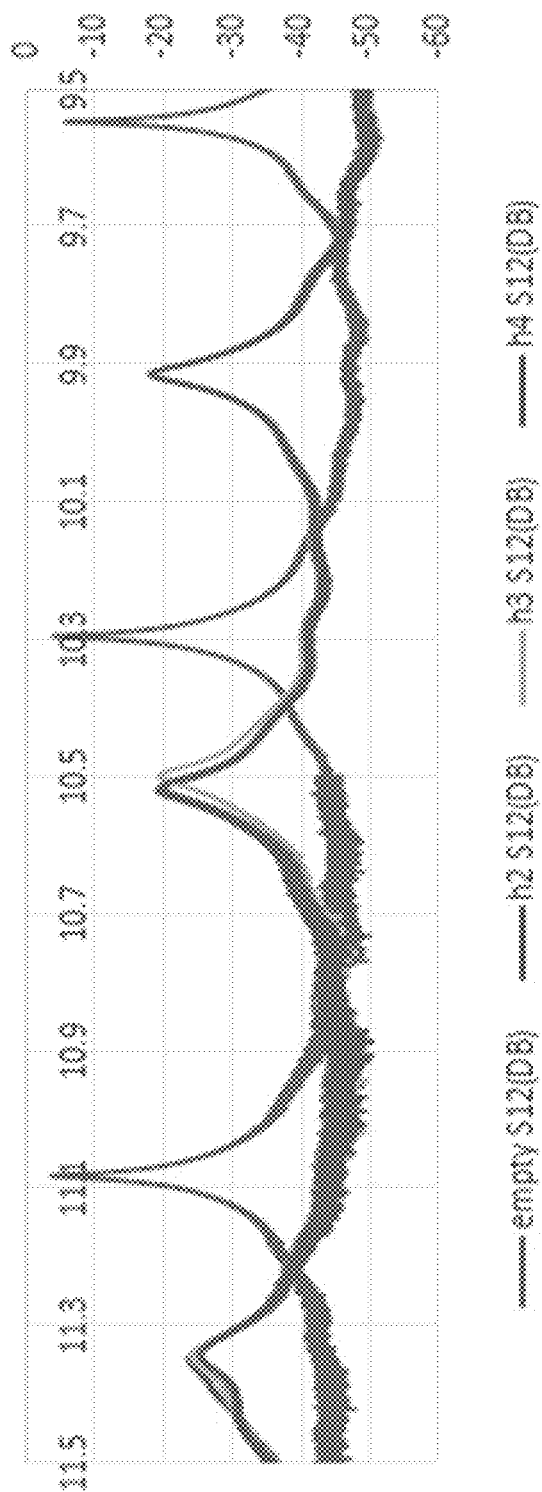
FIG. 6 shows the experimental results for the $S_{12}$ amplitude in the range of 9.0-11.5 GHz for the empty container and the diamonds H2, H3 and H4 inside the container.

Reference is now made to FIG. 6 showing the obtained experimental results for the $S_{12}$ amplitude in the range of 9.0-11.5 GHz for the empty container and the diamonds H2, H3 and H4 inside the container. The following table summarises the amplitude measurements for the S-parameters in the present experiment:

| | $S_{12}$ (A) | | |
|---|---|---|---|
| Max difference 2H-4H | 7.37789 | 4.729332 | 6.380294 |
| Median 2H-4H | 0.095913 | 0.108078 | 0.071402 |
| Min difference 2H-4H | −7.33505 | −4.57347 | −5.91056 |
| | $S_{12}$ (B) | | |
| Max difference 2H-4H | 7.483481 | 5.303044 | 6.38437 |
| Median 2H-4H | 0.08823 | 0.109761 | 0.079182 |
| Min difference 2H-4H | −7.35643 | −5.24752 | −5.88362 |
| | $S_{21}$ (A) | | |
| Max difference 2H-4H | 7.472784 | 5.246464 | 6.376903 |
| Median 2H-4H | 0.091312 | 0.095283 | 0.068593 |
| Min difference 2H-4H | −7.3609 | −3.78521 | −5.98847 |
| | $S_{21}$ (B) | | |
| Max difference 2H-4H | 7.470247 | 5.288277 | 6.392119 |
| Median 2H-4H | 0.073975 | 0.111156 | 0.101681 |
| Min difference 2H-4H | −7.37421 | −3.96676 | −6.43275 |

The following conclusions were made from this experiment:

The S-peak around 10 GHz frequency appears to be "clean" in all the measurements.

The size of the diamonds does not drastically affect the position of this peak, its measured amplitude and phase (there are no drastic changes in the measurements of the diamonds having different size).

Small changes in the position of this peak are nevertheless observed for different sizes of the diamonds. However, as mentioned above, the effect is not significant The examination of the median also shows that the distribution of both the intensity and the measured angle is very similar in the diamonds.

Experiment 3—Nitrogen Concentration

In order to check the effect of nitrogen concentration in the diamonds, the following diamonds of the different types, but having the same size, were subjected to the experiment:

Sample H10: Natural diamond weighing 0.40 carats with low nitrogen concentration.

Sample H21: Natural diamond weighing 0.40 carats with high nitrogen concentration (five times more than in H10).

Sample H22: Natural diamond weighing 0.40 carats with high nitrogen concentration (six times more than in H10).

These three diamonds were initially subjected to infrared (IR) spectroscopy. From the IR spectrum, the total nitrogen concentration was calculated for each of the diamonds, as well as nitrogen concentration in different crystal forms of these diamonds. Each crystal form of a particular diamond appears as a separate peak in the IR spectrum. The results are summarised in the following table:

| IR Peak, cm$^{-1}$ | H10 | H21 | H22 |
|---|---|---|---|
| 1370.00 | 0.00 | 0.24 | 0.40 |
| 1344.00 | 0.05 | 0.00 | 0.00 |
| 1331.00 | 0.07 | 0.32 | 0.47 |
| 1282.00 | 0.10 | 0.63 | 0.66 |
| 1282d | 0.04 | 0.33 | 0.24 |
| 1131.00 | 0.17 | 0.54 | 0.76 |

Then for each measurement with the device of the present embodiments, one point of experimentally measured frequency with amplitude was obtained. The peak at 9.9 GHz was chosen as a characteristic peak in the frequency domain range, and the results presented herein are focused around this peak.

Figure 7A:
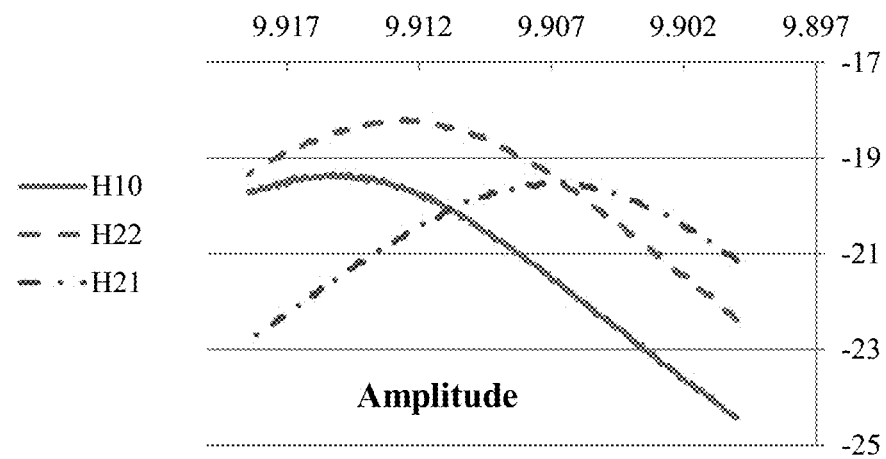
FIG. 7a shows the experimental $S_{12}$ amplitude around the characteristic peak of 9.9 GHz for the diamonds H10, H21 and H22.
Figure 7B:
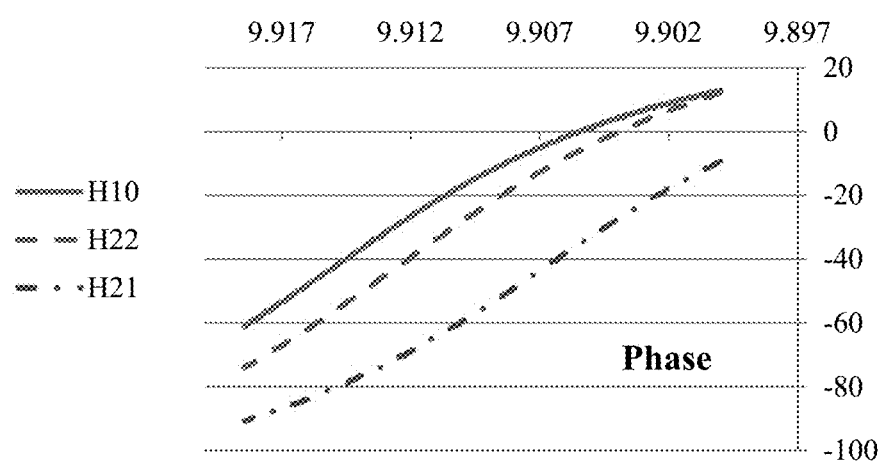
FIG. 7b shows the experimental $S_{12}$ phase around the characteristic peak of 9.9 GHz for the diamonds H10, H21 and H22.
Figure 7C:
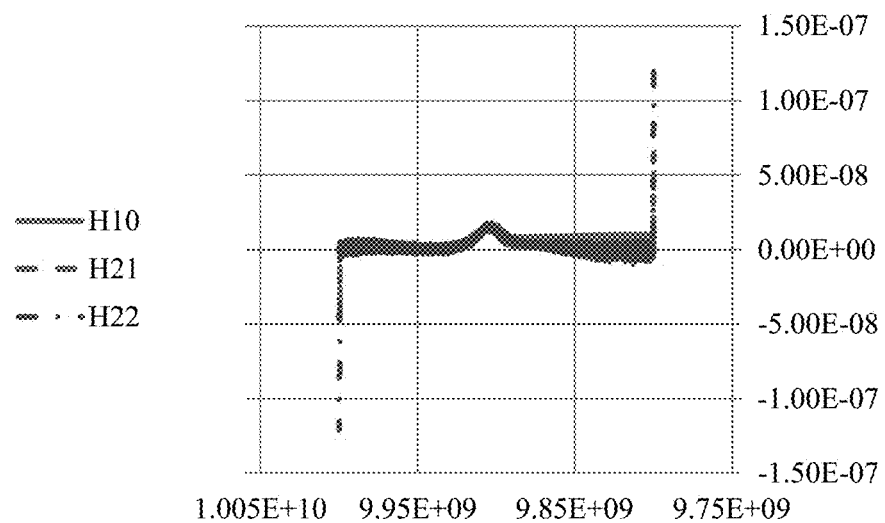
FIG. 7c shows the experimental group delay around the characteristic peak of 9.9 GHz for the diamonds H10, H21 and H22.
Figure 7D:
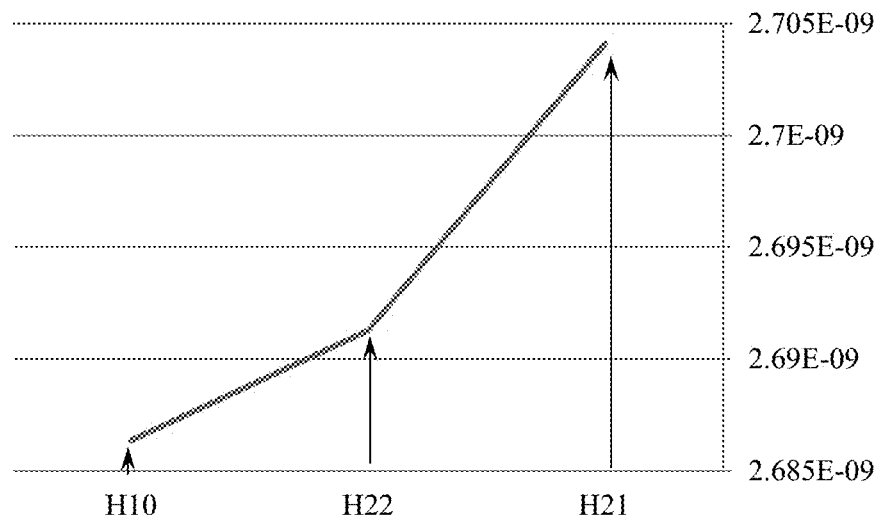
FIG. 7d shows the group delay average around the characteristic peak of 9.9 GHz for the diamonds H10, H21 and H22.

Reference is now made to FIGS. 7a and 7b showing the $S_{12}$ amplitude and phase, respectively, around the peak of 9.9 GHz for the three diamonds H10, H21 and H22. FIG. 7c shows the group delay around the characteristic peak of 9.9 GHz for these diamonds. FIG. 7d shows the group delay average around this peak.

The following conclusions were made from this experiment:

The $S_{12}$ phase graph demonstrates the almost linear relationship for the different diamonds. Because the diamonds have the same weight, only chemical composition of the diamonds (nitrogen concentration) can cause such difference between the phases.

The group delay and its approximate linearity can also be observed.

Experiment 4—Diamond Colour

In order to check the effect of the diamond colour, the following diamonds of the different colours, having the same size, were subjected to the experiment: H, M, D, H12 and L1. The container made of an electromagnetically transparent Platilon® polymer (ε=2.3) was used in the experiment. The waveguide used in the experiment was designed for the operation in the 12-18 GHz range.

Figure 8A:
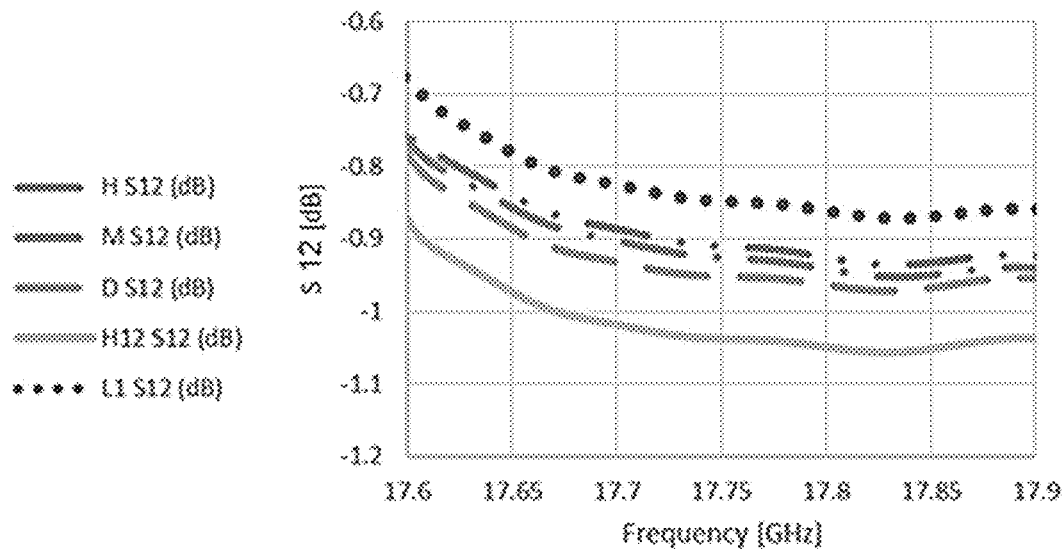
FIG. 8a shows the $S_{12}$ amplitude functions for each of the diamonds having different colour in the frequency range of 17.6-17.9 GHz.
Figure 8B:
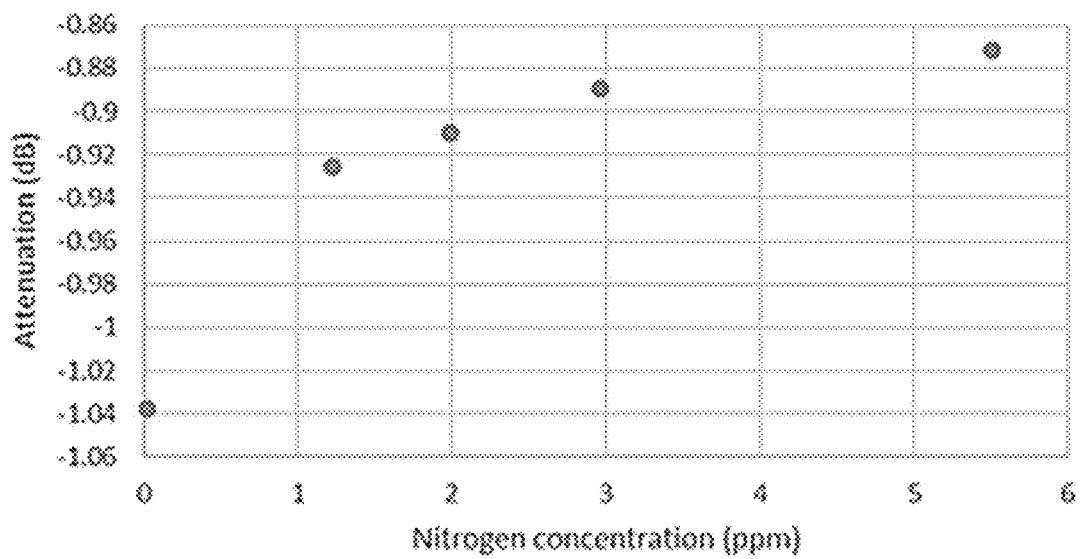
FIG. 8b shows the final correlation plot of attenuation versus nitrogen concentration in diamonds measured at 17.8 GHz.

For each point of experimentally measured frequency with amplitude (dB) was obtained. FIG. 8a shows the $S_{12}$ amplitude functions for each of the diamonds in the frequency range of 17.6-17.9 GHz. These graphs allow further calibration of the S-parameters for grading diamonds. FIG. 8b shows the final correlation plot of attenuation versus nitrogen concentration in diamonds measured at 17.8 GHz.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

The invention claimed is:

1. A method for grading a diamond comprising the steps of:
   a) placing the diamond to be graded into a grading device;
   b) Irradiating the diamond within the grading device with a radiofrequency (RF) signal in a frequency domain range of up to 3 THz;
   c) recording a modulated signal received from the diamond, after the irradiation and as a result of the radiation, in a form of S-parameters as a function of a parameter selected from the group consisting of frequency, complex dielectric constant, complex magnetic permeability, capacitance, inductance, resistance, reflectance, and absorbance;
   d) processing the recorded signal in the processing unit to obtain data containing information about either an amplitude, or phase, or both of the recorded S-parameters as a function of said parameter;
   e) performing calculations relating to mathematical analysis, calibration of the obtained data, displaying the calculated data in a readable format or plotting said data in a graphical form; and
   f) running a computer algorithm correlating said obtained data to either nitrogen concentration, boron concentration or plastic deformation in diamonds, thereby allowing grading of the diamond,
   wherein the grading of the diamond comprises colour identification of said diamond according to the GIA diamond colour scale, detection of plastic deformations in said diamond and determining whether said diamond is natural, treated or synthetic.

2. The method of claim 1, wherein the RF signal is a sweeping sine waveform signal.

3. The method of claim 1, wherein the RF signal has a single frequency, at which said obtained data show the most pronounced dependence on either nitrogen or boron concentration, or on plastic deformations in diamonds.

4. A grading device for grading a diamond, said device is designed to operate in a radiofrequency (RF) range and comprises:
   a) a radiofrequency (RF) signal generator configured to generate a signal in a frequency range of 0 to 3 THz and output said signal to a transmitting antenna;
   b) the transmitting antenna connected to said generator via an electric cable and configured to transmit said signal into a waveguide, cavity or resonator;
   c) said waveguide, cavity or resonator designed to accommodate the diamond, to receive the signal from the transmitting antenna and to transmit said signal through the diamond to a receiving antenna, wherein the signal transmitted to the receiving antenna is a signal modulated by the diamond;
   d) the receiving antenna connected to an amplitude and frequency detector via an electric cable and configured to receive the modulated signal from the waveguide, cavity or resonator;
   e) the amplitude and frequency detector configured to detect the modulated signal received from the receiving antenna and transmit said modulated signal to a computing unit; and
   f) the computing unit configured to receive the modulated signal from the amplitude and frequency detector, to convert said signal into computer data containing information about the amplitude and phase of said signal, to perform calculations relating to mathematical analysis and calibration of the data, to display said data in a readable format or to plot said data in a graphical form, and to run algorithm correlating the data with either nitrogen concentration, boron concentration or plastic deformation in diamonds, thereby allowing to grade the diamond.

5. The device of claim 4, wherein the RF signal is a sweeping sine waveform signal.

6. The device of claim 4, wherein the RF signal has a single frequency, at which said obtained data show the most pronounced dependence on either nitrogen or boron concentration, or on plastic deformations in diamonds.

7. The device of claim 4, wherein said modulated signal is in a form of S-parameters as a function of frequency or any other parameter, such as complex dielectric constant, complex magnetic permeability, capacitance, inductance, resistance, reflectance, absorbance, or any other quantity that can be deduced by irradiation of the diamond.

8. The device of claim 7, wherein said S-parameters are $S_{12}$ or $S_{21}$ amplitude or phase.

9. The device of claim 4, wherein the computer algorithm is designed to correlate said S-parameters to either nitrogen or boron concentration, or to plastic deformation in diamonds, thereby allowing grading the diamond.

10. The device of claim 4, further comprising a quadrature (I/Q) demodulator.

11. The device of claim 4, wherein said resonator is a closed resonator with a container for placing the diamond.

12. The device of claim 11, wherein said closed resonator has a cavity or internal container for placing the diamond.

13. The device of claim 4, wherein said device is a capacitor capable of measuring capacitance of the diamond to be placed inside said capacitor and graded, said capacitance is an indicator of nitrogen or boron concentration or of plastic deformation in the diamond crystal.

14. The device of claim 4, wherein said device is an inductance coil capable of measuring inductance of the diamond to be placed inside said inductance coil and graded, said inductance is an indicator of nitrogen or boron concentration or of plastic deformation in the diamond crystal.

* * * * *